United States Patent [19]

Polaschegg et al.

[11] Patent Number: 5,178,179
[45] Date of Patent: Jan. 12, 1993

[54] PRESSURE EQUALIZING VESSEL FOR A HEMODIALYSIS CONCENTRATE

[75] Inventors: Hans-Dietrich Polaschegg, Oberursel/Ts.; Wendelin Backhaus, Kronberg; Joachim Manke, Löhnberg; Walter Pieper, Florstadt; Hans Walter, Offenbach, all of Fed. Rep. of Germany

[73] Assignee: Fresenius AG, Bad Homburg, Fed. Rep. of Germany

[21] Appl. No.: 579,641

[22] Filed: Sep. 10, 1990

[30] Foreign Application Priority Data

Sep. 9, 1989 [DE] Fed. Rep. of Germany ....... 3930181

[51] Int. Cl.⁵ .................. A61M 1/14; G01F 23/00
[52] U.S. Cl. ............................ 137/240; 137/392; 604/65; 73/304 R
[58] Field of Search .......... 137/340, 386, 392; 604/65, 67; 73/304 R; 134/166 R, 166 C, 168 C, 169 C; 210/80, 87, 90

[56] References Cited

U.S. PATENT DOCUMENTS

| | | | |
|---|---|---|---|
| 3,596,673 | 8/1971 | Laucournet | 137/392 |
| 4,085,046 | 4/1978 | Saporito, Jr. | 210/90 |
| 4,231,366 | 11/1980 | Schael | 604/67 |
| 4,483,463 | 11/1984 | Buschmann | 137/392 |
| 4,681,563 | 7/1987 | Deckert et al. | 604/67 |
| 4,717,548 | 1/1988 | Lee | 604/67 |
| 4,747,822 | 5/1988 | Peabody | 604/65 |
| 4,797,655 | 1/1989 | Orndal et al. | 604/67 |
| 4,832,689 | 5/1989 | Maurer et al. | 604/67 |

FOREIGN PATENT DOCUMENTS 3734880 3/1989 Fed. Rep. of Germany.

Primary Examiner—George L. Walton
Attorney, Agent, or Firm—Townsend and Townsend

[57] ABSTRACT

This invention relates to a pressure equalizing vessel for a hemodialysis concentrate. To ensure the supply of concentrate at a constant pressure to the concentrate pump for preparing dialysis fluid, even in cases where a central concentrate supply system is used, the present invention suggests that a cylindrical upright vessel 1 whose lower portion is provided with a concentrate inlet and whose upper portion has arranged thereon a venting means 4 should have inserted thereinto a concentrate suction tube 7 which is equipped with at least one level sensor (FIG. 1).

12 Claims, 1 Drawing Sheet

PRESSURE EQUALIZING VESSEL FOR A HEMODIALYSIS CONCENTRATE

BACKGROUND OF THE INVENTION

The present invention relates to a pressure equalizing vessel used for a hemodialysis concentrate and comprising a substantially cylindrical upright vessel at the lower end of which a concentrate inlet provided with a valve is arranged and the upper portion of which is equipped with a venting means, said vessel comprising a conduit arranged on the upper portion thereof for discharging concentrate to a hemodialysis device.

During hemodialysis the dialysis fluid is normally prepared by mixing dialysis concentrate with water.

There are two different methods for producing or preparing dialysis fluid:

In the first method mixing is carried out by means of a volumetric mixing method wherein water and concentrate are intermixed at a given predetermined volumetric ratio, e.g. a ratio of 1:34.

A second method for preparing dialysis fluid is the conductivity-controlled method wherein the ratio of the water and concentrate flow is adjusted such that a specific conductivity is obtained in the finished dialysis fluid.

The dialysis fluid is typically prepared from one or two concentrates and water. However, it is also possible to prepare the dialysis fluid from more than two concentrates and from water.

In practice, the dialysis concentrate is provided in two different ways. On the one hand, it is possible to provide the dialysis concentrate in the conventional way, i.e. in canisters, to suck it in, using a concentrate pump of the hemodialysis device, and to supply it to a mixing means in which the dialysis concentrate is mixed with prepared water. This kind of preparing dialysis fluid permits a certain flexibility when the composition of the dialysis fluid is chosen, but requires considerable efforts, as the canisters must be transported, provided and disposed of. Furthermore, it is always necessary to suitably connect the canisters to a concentrate suction conduit. This may result in malfunctions. The disposal of the empty canisters poses considerable problems because of the resultant waste as such and because of the relatively large volume of the empty canisters.

Central concentrate supply systems have therefore been developed wherein the concentrates are delivered under pressure from a central container to respective tapping or connecting points of the hemodialysis device.

The concentrate pumps which are normally used in hemodialysis devices are so constructed that their delivery rate depends on the input pressure. It is therefore necessary to equalize the normally varying pressure of a central concentrate supply system, so that the delivery rate of the mixing pump is not impaired by pressure variations. Pressure equalizing containers have therefore been designed which consist of a ventilable vessel and a level regulating system. For instance, float switches are used for actuating a concentrate inlet valve and/or a valve in an outlet conduit leading to the hemodialysis device.

The prior art discloses pressure equalizing containers which comprises a connection for a concentrate suction conduit at the side of the equalizing vessel or in the bottom thereof. However, the concentrate suction conduit may also be designed in the form of a suction tube which can be introduced into a concentrate canister, as is known from German patent application 37 34 880.

SUMMARY OF THE INVENTION

It is the object of the present invention to provide a pressure equalizing vessel of the above-mentioned type which is simple in construction and reliable during operation and which guarantees pressure equalization during supply of the hemodialysis concentrate and permits the connection of the hemodialysis device to a central concentrate supply system.

In accordance with the invention, this object is attained in that a concentrate suction tube which is provided with at least one level sensor is arranged in the cylindrical vessel.

Other advantageous developments of the invention will become apparent from the sub-claims.

The pressure equalizing vessel of the invention is characterized by several considerable advantages. In accordance with the invention, it is possible to equalize the pressure and to ensure a specific level of the hemodialysis concentrate at the same time. In accordance with the invention, it is above all possible to use the level measuring means contained in or associated with the concentrate suction tube for controlling the level in the pressure equalizing vessel.

The pressure equalizing vessel of the invention comprises a substantially cylindrical upright vessel which is adapted to the length of the concentrate suction tube. The cylindrical tube is closed at the bottom and laterally comprises an inlet for the concentrate supply. The upper portion of the cylindrical vessel is open, so that the concentrate suction tube may be inserted. In the inserted state this concentrate suction tube covers the opening, so that foreign matter is prevented from penetrating into the cylindrical vessel. In cases where the concentrate suction tube has been removed, the cylindrical vessel may be closed by a cover. Furthermore, an air vent hole which is advantageously closed by means of a hydrophobic membrane is provided in the upper portion of the cylindrical vessel.

The inlet conduit which is contained in the bottom portion of the cylindrical vessel can preferably be opened or closed by means of a valve. The control means of the hemodialysis device makes it possible to control the valve on the basis of a signal from the level sensor, which is integrated in the suction tube, in such a way that the concentrate fluid level remains approximately constant and is kept as low as possible.

If only one level sensor which has a single switching threshold is used in the pressure equalizing vessel of the invention, the fluid level varies around this switching threshold.

In accordance with the invention, there is preferably provided an alarm means which is actuated if after opening of the concentrate inlet valve the switching threshold of the level sensor is not exceeded within a specific time interval. The valve is here closed to draw the user's attention to some kind of failure.

Such a failure may be an interruption of the concentrate flow, in which case the aperture equalizing vessel is no longer filled in an adequate way, or it may be a defective level sensor. In the latter case the hydrophobic membrane would be clogged by the concentrate, so that an adequate venting operation would no longer be possible.

As for the level sensor integrated in the suction tube, it is possible to construct the sensor as described in German patent application 37 34 880.

In accordance with the invention, it is possible to design the level sensor, as known, in the form of a conductivity sensor. The level sensor may however also be formed as a fiber-optical sensor, e.g. for detecting or measuring the optical rotation of the concentrate or the level in the known way through total reflection. However, it is also possible to design the level sensor as a density sensor or as a vibration sensor.

In an especially advantageous embodiment of the invention, the cylindrical vessel is shaped in the form of a vessel which is integrated in the hemodialysis device and by means of which the suction tube can be disinfected and cleansed in the disinfecting and cleansing phase. This design has the decisive advantage that no additional vessel has to be used, as the already known disinfecting and cleansing vessel can simultaneously be used as a pressure equalizing vessel after corresponding modifications.

In the latter case it is necessary to provide two additional connection conduits on the cylindrical vessel. These connection conduits can be opened or closed via valves. The supply conduit and the discharge conduit, respectively, serve to supply or discharge cleansing liquid.

In the last-mentioned case it is especially advantageous when the pressure equalizing vessel is so connected in the dialysis fluid circuit that it is arranged downstream of the dialyzer, i.e. in front of a possible recirculation circuit.

The supply conduit and the discharge conduit, respectively, are arranged such that the cylindrical vessel can be flushed by the cleaning liquid entirely or in a secondary flow and that the cleansing liquid can simultaneously be sucked in by the concentrate pump. In the disinfecting and cleansing phase the valve in the concentration liquid supply conduit remains closed. Furthermore, the level measuring conduit is shut off. During dialysis the two valves are closed during supply and discharge of the cleansing liquid, while the valve in the concentrate supply conduit is open.

In another, particularly advantageous embodiment of the invention, a sensing means is arranged on the pressure equalizing vessel for detecting whether the concentrate suction tube has correctly been inserted into or fixed to the cylindrical vessel. The sensing means may e.g. comrpise a magnetic switch which is operated by a magnet fixed to the concentrate suction tube. The magnetic switch or the sensing means may be connected to the control means in such a way that the concentrate inlet valve can only be operated when the concentrate suction tube is correctly arranged.

In the last-mentioned application where the cylindrical vessel may simultaneously serve disinfecting or cleansing purposes, it is possible to leave the central concentrate supply system in a permanently connected state. It is possible without any mechanical operations, i.e. without rearranging tube connections, or the like, to carry out dialysis and to flush or disinfect the dialysis device thereafter and thus to prepare it for the next hemodialysis operation.

In addition, it is possible to introduce the concentrate suction tube into a canister for providing concentrate fluid.

BRIEF DESCRIPTION OF THE DRAWINGS

The present invention shall now be described with the aid of two embodiments with reference to the drawings, in which.

DESCRIPTION OF THE PREFERRED EMBODIMENTS

Figure 1:
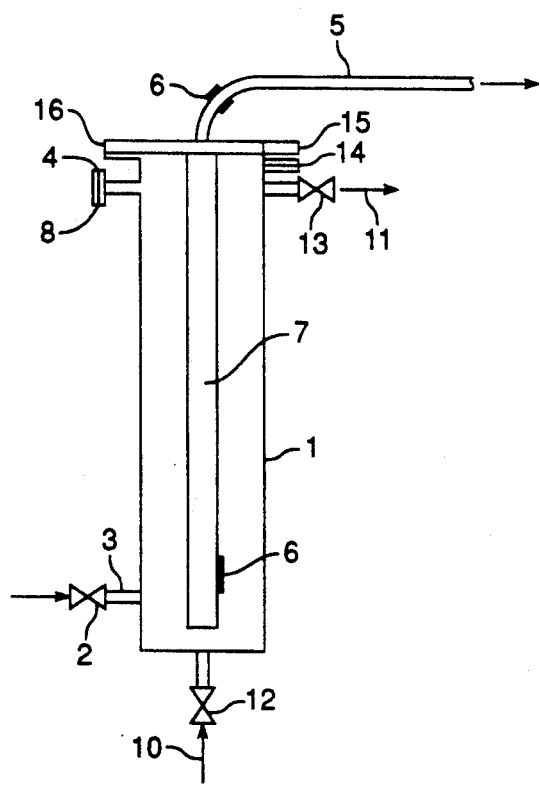
FIG. 1 is a schematic side view of a first embodiment of the pressure equalizing vessel of the invention.

FIG. 1 shows a substantially cylindrical vessel 1 the bottom proton of which is provided with an inlet conduit 3 for supplying concentrate; the inlet conduit can be closed by means of a valve 2. Furthermore, a supply conduit 10 for supplying flushing liquid is arranged in the bottom portion, which supply conduit can be closed by means of a valve 12.

In the upper portion the cylindrical vessel 1 comprises a venting means 4 in which a hydrophobic filter 8 is arranged. Furthermore, a discharge conduit 11 for discharging flushing liquid is connected to the upper portion. The discharge conduit can be closed via a valve 13.

A concentrate suction tube 7 which is connected to a cover 16 or a flange and communicates with a conduit 5 for discharging fluid can be inserted into the cylindrical vessel 1. Conduit 5 is normally connected to a hemodialysis device.

In the illustrated embodiment, level sensors 6 which serve to determine the fluid quantity in the cylindrical vessel 1 and to adjust it to a given fluid level are provided in the area of the concentrate suction tube 7 or conduit 5. The level sensors 6 are e.g. designed in the form of conductivity sensors.

Furthermore, cover 16 has secured thereto a magnet 15 which serves to actuate a magnetic switch 14 with the aid of which the exact positioning of the concentrate suction tube 7 can be determined.

During dialysis valve 2 is temporarily open to introduce a sufficient amount of fluid into the cylindrical vessel 1. The fluid is discharged through conduit 5; valves 12 and 13 remain closed. In the flushing phase valve 2 is closed, while valves 12 and 13 are open, so that a flushing liquid can be fed into the cylindrical vessel 1 and discharged via both conduit 5 and discharge conduit 11.

Figure 2:
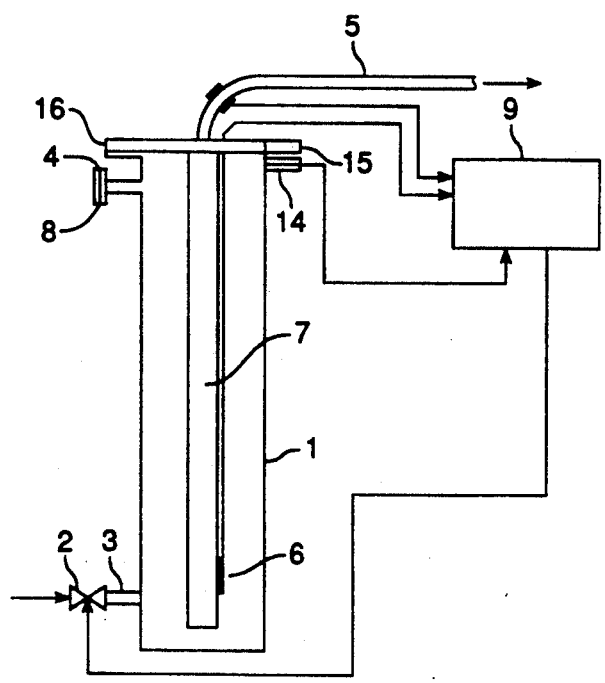
FIG. 2 is a schematic illustration of a second embodiment of the pressure equalizing vessel of the invention.

The embodiment shown in FIG. 2 substantially corresponds to the embodiment illustrated in FIG. 1, but differs therefrom in that no discharge conduit 11 and no supply conduit 10 are provided for a flushing liquid.

Furthermore, FIG. 2 shows a control means 9 which suitably communicates with level sensors 6, magnetic switch 14 and valve 2 to ensure the above-described operation of the pressure equalizing vessel.

The present invention is not limited to the illustrated embodiments. Rather, many variations and modifications may be made within the scope of the invention.

We claim:

1. A pressure equalizing vessel for equalizing pressure of a hemodialysis concentrate supplied to concentrate pump means of a plurality of hemodialysis devices by a central concentrate supply system, the concentrate being subject to supply pressure variations from said supply system, the pressure equalizing vessel comprising a substantially cylindrical upright vessel (1) whose lower portion has a arranged thereon a concentrate inlet (3) provided with a valve (2) and whose upper portion is equipped with a venting means (4), said vessel including a conduit (5) arranged on the upper portion thereof for discharging concentrate to the concentrate pump means of the hemodialysis devices, wherein a concentrate suction tube (7) with at least on level sensor (6) responsive to variations in the level of concentrate within the vessel is arranged in said cylindrical vessel (1) and wherein said valve (2) disposed in the concentrate inlet (3) is actuated by a control means (9) in response to signals from said level sensor (6), wherein pressure of the concentrate is equalized by venting through said venting means (4) and maintaining a substantially constant level of the concentrate within the vessel by said valve (2) actuated by said control means (9) in response to signals from said level sensor (6).

2. The pressure equalizing vessel as set forth in claim 1, wherein said concentrate suction tube (7) can be withdrawn from said cylindrical vessel (1) and said cylindrical vessel (1) can be closed by means of a cover.

3. The pressure equalizing vessel as set forth in claim 1 or 2, wherein said venting means (4) is provided in the upper portion of said cylindrical vessel (1).

4. The pressure equalizing vessel as set forth in claim 3, wherein said venting means (4) is closed by a hydrophobic filter (8).

5. The pressure equalizing vessel as set forth in claims 1, 2, 3 or 4, wherein said level sensor (6) is designed in the form of a conductivity sensor.

6. The pressure equalizing vessel as set forth in claims 1, 2, 3 or 4, wherein said level sensor (6) is designed in the form of a fiber-optical sensor.

7. The pressure equalizing vessel as set forth in claims 1, 2, 3 or 4, wherein said level sensor (6) is designed in the form of a vibration sensor.

8. The pressure equalizing vessel as set forth in any of claims 1 to 7, wherein said cylindrical vessel (1) is shaped in the form of a vessel which is integrated in said hemodialysis device and by means of which said suction tube (7) can be disinfected and cleansed in the disinfecting and cleansing phase.

9. The pressure equalizing vessel as set forth in claim 8, wherein said cylindrical vessel (1) is provided with a flushing liquid supply conduit (10) and a flushing liquid discharge conduit (11) which have arranged therein valves (12, 13) and which are connected in the dialyzing liquid circuit, wherein opening of valves (12, 13) causes a flushing liquid to flow through the concentrate suction tube (7) for cleansing thereof.

10. The pressure equalizing vessel as set forth in claim 8, wherein said supply conduit (10) and said discharge conduit (11) are provided on opposite portions of said cylindrical vessel (1).

11. The pressure equalizing vessel as set forth in claims 1, 2, 3 or 4, wherein a sensing means is provided for sensing the proper arrangement of said concentrate suction tube (7) on said cylindrical vessel (1).

12. The pressure equalizing vessel as set forth in claim 11, wherein said sensing means comprises a magnetic switch (14).

* * * * *